United States Patent

Chetcuti

[11] Patent Number: 5,393,606
[45] Date of Patent: Feb. 28, 1995

[54] CHARGE-TRANSFER COMPLEXES WITH N-AROMATIC COMPOUNDS, THE PREPARATION THEREOF AND THE USE THEREOF

[75] Inventor: Peter Chetcuti, Basel, Switzerland
[73] Assignee: Ciba-Geigy Corporation, Ardsley, N.Y.
[21] Appl. No.: 67,206
[22] Filed: May 25, 1993

[30] Foreign Application Priority Data

Jun. 3, 1992 [CH] Switzerland ............... 1775/92-8

[51] Int. Cl.⁶ .................. B32B 33/00; C08K 5/34; C08K 5/17; H01B 1/06
[52] U.S. Cl. .................. 428/332; 428/334; 428/335; 428/336; 428/357; 524/99; 524/100; 524/102; 524/237; 524/254; 252/510; 252/511
[58] Field of Search ............... 524/195, 237, 241, 242, 524/254, 255, 257, 99, 100, 102; 252/500, 510, 511; 428/357, 332, 334

[56] References Cited

U.S. PATENT DOCUMENTS

5,009,812  4/1991  Finter et al. ............... 252/500

FOREIGN PATENT DOCUMENTS

0285564  3/1988  European Pat. Off.

OTHER PUBLICATIONS

Synthetic Metals, 36 (1990) 65–73 M. Forkner et al.
S. Hünig et al. Advanced Materials (1991) pp. 225–235.
Synthetic Metals, 27 (1988) L. Miller et al. B431–B437.
J. Heterocyclic Chem. vol. 26 pp. 435–438 Sugimoto et al.
Synthetic Metals 41–43 (1991) pp. 2364–2375 S. Rak et al.
Chem. Mater. vol. 2, 1990 pp. 339 & 340.
Synthetic Metals, vol. 24 (1988) pp. 107–114 A. Tracy et al.
J. Am. Chem. Soc. 102 #17 (1980) pp. 5436–5442, C. Jaeger et al.
J. Am. Chem. Soc. 104, (1982) pp. 7581–7585 K. Dietz et al.
Canadian Journal of Chem. vol. 43 (1965) pp. 1448–1453, L. R. Melby.

Primary Examiner—Tae H. Yoon
Attorney, Agent, or Firm—George R. Dohmann

[57] ABSTRACT

Charge-transfer complexes of formula I $$(A^{\ominus})_n B^{n\oplus} \qquad (I)$$

wherein
a) n is 1 or 2,
b) A is the radical anion of a compound of formula II or of a mixture of compounds of formula II

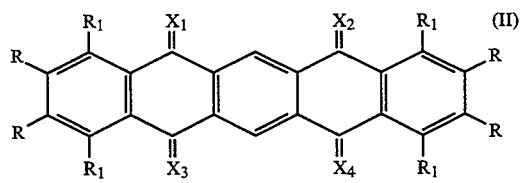

wherein the substituents R are the same and are H or $C_1$–$C_4$alkyl, or adjacent substituents R together form —$(CH_2)_3$— or —$(CH_2)_4$—;
$R_1$ is H or $C_1$–$C_4$alkyl;
$X_1$ is =N—CN;
and $X_2$, $X_3$ and $X_4$ are =O or =N—CN, and
c) when n=1, B is the monovalent radical cation and when n=2, B is the divalent radical cation of an N-aromatic compound having a total of from 1 to 5 aromatic rings that are unsubstituted or substituted by halogen, $C_1$–$C_4$alkyl or by $C_1$–$C_4$alkoxy, at least one ring containing at least one group —$NR_2$— or [=$N^+R_2$—] $I^-$ wherein $R_2$ is $C_1$–$C_4$alkyl or benzyl.

The complexes are electrical conductors with which plastics materials may be antistatically treated or converted into electrical conductors.

24 Claims, No Drawings

CHARGE-TRANSFER COMPLEXES WITH N-AROMATIC COMPOUNDS, THE PREPARATION THEREOF AND THE USE THEREOF

The invention relates to charge-transfer complexes (hereinafter abbreviated to CT complexes) comprising pentacenecyanoimine derivatives as electron acceptors and nitrogen-aromatic compounds as electron donors; to a process for the preparation thereof; to compositions comprising a plastics material and such a CT complex; and to the use of the CT complexes as electrical conductors, for example for the preparation of electrically conductive films, foils or coatings.

Synthetic Metals, 41–43, pages 2365 to 2375 (1991) describes a powdered CT complex comprising tetracyanoiminepentacene and tetrathiofulvalene as electron donor, as well as individual crystals of tetracyanoiminepentacene and alkali metal cations and tetraalkylammonium.

Moreover, 5,7,12,14-tetracyanoiminepentacene is described by L. Miller et al. in Chem. Mater. 2, pages 339–340 (1990) as an electron acceptor for the preparation of radical cation salts with alkali metals, for example sodium and potassium.

U.S. Pat. No. 5,009,812 describes antistatically treated, electrically conductive polymers which comprise, for example, CT complexes of tetrathio-, tetraseleno- or tetratelluro-tetracenes as electron donors and halogens or oxygen as electron acceptors. The CT complexes in those materials form needle networks in the polymer matrix.

CT complexes of tetracyanoquinodimethane (TCNQ) as electron acceptor and N-containing aromatic compounds as donors are described, for example, by C. D. Jaeger and A. J. Bard in J. Am. Chem. Soc., Vol. 102, No. 17, pages 5435–5442 (1980) and by L. Russell Melby in Can. J. Chem., Vol. 43, pages 1448–1453 (1965). Those CT complexes do not always crystallise in the form of needles, and on account of their crystal form they are not suitable for the preparation of electrically conductive foils comprising a network of crystal needles.

It has now been found that pentacenecyanoimines and certain N-aromatic compounds surprisingly form CT complexes that unexpectedly crystallise in the form of needles even in the presence of binders, have a high electrical conductivity and exhibit virtually no corrosive action on the metal parts of processing machines. The starting compounds are also soluble in less polar organic solvents, so that it is not necessary to use very high temperatures for the preparation of the CT complexes. The CT complexes exhibit an unexpectedly high stability with respect to moisture and heat. Moreover, the CT complexes surprisingly form fine, stable crystal needles, as a result of which films or foils having very fine-meshed needle networks and high electrical conductivity are obtained.

The invention relates to CT complexes of formula I $$(A^{\ominus})_n B^{n\oplus} \qquad (I)$$

wherein
a) n is 1 or 2,
b) A is the radical anion of a compound of formula II or of a mixture of compounds of formula II

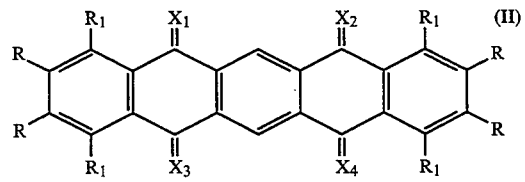

wherein the substituents R are the same and are H or $C_1$–$C_4$alkyl, or adjacent substituents R together form —$(CH_2)_3$— or —$(CH_2)_4$—;
$R_1$ is H or $C_1$–$C_4$alkyl;
$X_1$ is =N—CN; and
$X_2$, $X_3$ and $X_4$ are =O or =N—CN, and c) when n=1, B is the monovalent radical cation and when n=2, B is the divalent radical cation of an N-aromatic compound having a total of from 1 to 5 aromatic rings that are unsubstituted or substituted by halogen, $C_1$–$C_4$alkyl or by $C_1$–$C_4$alkoxy, at least one ring containing at least one group —$NR_2$— or [=$N^+R_2$—] $I^-$ wherein $R_2$ is $C_1$–$C_4$alkyl or benzyl.

When R and $R_1$ are alkyl, they may be methyl, ethyl, n-propyl, isopropyl, n-butyl, isobutyl or tert-butyl. Preferred alkyl radicals are methyl and ethyl. In a preferred embodiment, the substituents R are $C_1$–$C_4$alkyl and the substituents $R_1$ are H, or the substituents $R_1$ are $C_1$–$C_4$alkyl and the substituents R are H. Preferably, R and $R_1$ are H, methyl or ethyl. In an especially preferred embodiment, R and $R_1$ are H.

In another preferred embodiment, $X_1$ and $X_4$ are =N—CN and $X_2$ and $X_3$ are =O or =N—CN, or $X_2$ and $X_3$ are =N—CN and $X_4$ is =O or =N—CN. Especially preferably, $X_1$, $X_2$, $X_3$ and $X_4$ are =N—CN.

Alkyl may be linear or branched. Examples are methyl, ethyl, n-propyl, isopropyl, n-butyl, isobutyl and tert-butyl. $R_2$ is preferably methyl or ethyl; $R_2$ is especially preferably methyl.

The mono- or di-valent radical cations B may be N-heterocyclic rings having one or two N atoms.

B preferably contains a total of from 1 to 3 and at least one N-aromatic ring. In a preferred embodiment, B contains from 1 to 3 rings and one heteroaromatic ring, or B is a bis-N-heteroaromatic ring. The rings are preferably 6-membered. Especially preferred N-aromatic compounds are pyridine, pyrimidine, pyrazine and phenazine.

In an especially preferred embodiment, B in formula I corresponds to cations of formulae IIIa to IIIf:

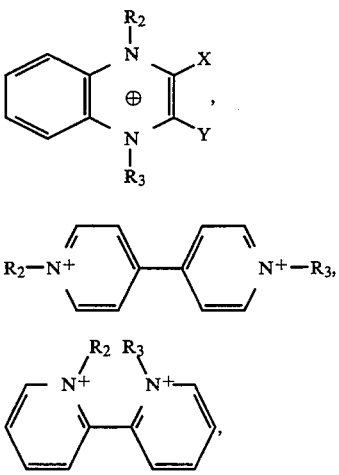

wherein
Y₁ is N or CH, and
X, X', Y and Y' are H, or
X and Y and/or X' and Y' are the group —CH═CH—CH═CH—, and
R₃ independently has the same meaning as R₂.

B in formula I may be, for example, cations of N-methyl- and N-ethyl-pyridinium; N-methyl- and N-ethyl-pyrazinium; N-methyl- and N-ethyl-quinolinium; N-methyl- and N-ethyl-phthalazinium; N-methyl- and N-ethyl-isoquinolinium; N-methyl- and N-ethyl-benzopyrazinium; 4,4'-dimethyl-, 4,4'-diethyl- and 4-methyl-4'-ethyl-bipyridinium; N-methyl- and N-ethyl-acridinium; N-methyl- and N-ethyl-phenazinium; 2,2'-dimethyl-, 2,2'-diethyl- and 2-methyl-2'-ethyl-bipyridinium; N-methyl- or N-ethyl-pyridazinium; 5,10-dimethyl-, 5,10-diethyl- or 5-methyl-10-ethyl-5,10-dihydrophenazinium.

The compound of formula II is preferably 5,7,12,14-tetracyanoiminepentacene which is in pure form or which comprises up to 10% by weight, based on the total mixture, of compounds of formula II wherein one or two cyanoimine groups have been replaced by oxygen. Especially preferred CT complexes of formula I are those comprising 5,7,12,14-tetracyanoiminepentacene and N-methylpyrazinium, N-ethylpyrazinium, 5,10-dimethyl-5,10-dihydrophenazinium, N-methylquinolinium, N-methylisoquinolinium or N-methylbenzopyridazinium as B.

The invention relates also to a process for the preparation of CT complexes of formula I, which comprises reacting one equivalent of a neutral 5,10-dihydrophenazine derivative or the iodine salt thereof as B, or the iodine salt of an N-aromatic compound B, with at least one equivalent of a pentacenecyanoimine of formula II in an inert organic solvent. It may, however, be advantageous to use an excess of the pentacenecyanoimine.

The N-aromatic compounds B are known in the form of salts or free bases, some being available commercially, or they can be prepared according to generally known processes. Reaction between the neutral base B and the alkyl iodide yields the desired iodine salt. The preparation of some of these derivatives is described by L. Russell Melby in Can. J. Chem., Vol. 43, pages 1448 to 1453 (1965).

The preparation of 5,7,12,14-tetracyanoiminepentacene is described by L. L. Miller in Synthetic Metals, 41–43, pages 2365–2375 (1991). The unsubstituted or substituted 5,7,12,14-pentacenetetrones used as starting compounds are obtainable according to a process described by W. H. Mills et al. in J. Chem. Soc. 101, page 2194 (1912). The 5,7,12,14-tetracyanoiminepentacenes can be purified by customary methods, for example by recrystallisation or by chromatographic methods. If no particular protective measures are taken, for example anhydrous conditions, cyanoimine groups may be replaced by oxygen, which does not adversely affect the formation of the desired CT complexes.

The process according to the invention is advantageously carried out at elevated temperatures, for example at from room temperature to 150° C. For the purpose of isolating the CT complexes according to the invention, the reaction mixture may be cooled and the resulting crystals filtered off and purified by washing and/or by recrystallisation.

Suitable solvents are, for example, non-polar, polar and aprotic solvents, which may be used alone or in mixtures comprising at least two solvents. Examples are: ethers (anisole, dibutyl ether, tetrahydrofuran, dioxane, ethylene glycol monomethyl or dimethyl ether, ethylene glycol monoethyl or diethyl ether, diethylene glycol diethyl ether, triethylene glycol dimethyl ether), halogenated hydrocarbons (methylene chloride, chloroform, 1,2-dichloroethane, 1,1,1-trichloroethane, 1,1,2,2-tetrachloroethane), carboxylic acid esters and lactones (ethyl acetate, propionic acid methyl ester, benzoic acid ethyl ester, 2-methoxyethyl acetate, γ-butyrolactone, δ-valerolactone, pivalolactone), carboxylic acid amides and lactams (N,N-dimethylformamide, N,N-diethylformamide, N,N-dimethylacetamide, tetramethylurea, hexamethylphosphoric acid triamide, γ-butyrolactam, ε-caprolactam, N-methylpyrrolidone, N-acetylpyrrolidone, N-methylcaprolactam), ketones (methyl ethyl ketone, methyl isobutyl ketone), sulfoxides (dimethyl sulfoxide), sulfones (dimethylsulfone, diethylsulfone, trimethylenesulfone, tetramethylenesulfone), tertiary amines (N-methylpiperidine, N-methylmorpholine), substituted benzenes (benzonitrile, chlorobenzene, o-dichlorobenzene, 1,2,4-trichlorobenzene, nitrobenzene, toluene, xylene), nitriles (acetonitrile, propionitrile) and aliphatic or cycloaliphatic hydrocarbons (petroleum ether, pentane, hexane, cyclohexane and methylcyclohexane). Also suitable are aromatic-aliphatic ethers, for example methyl- or ethyl-phenyl ether.

Polar solvents are preferred, because the iodine salts of compounds B are more readily soluble under those conditions. Preferred polar solvents are, for example, dimethylformamide and γ-butyrolactone.

The CT complexes obtainable by the process according to the invention are obtained in a high degree of purity and after filtration need only be washed with solvents. They are generally in the form of dark-coloured needle-like crystals which, in the form of a moulding, have an electrical conductivity of more than $1 \cdot 10^{-4}$ S/cm. They are excellently suitable as electrical conductors. For example, by incorporating those CT complexes into plastics materials, it is possible, depending on the nature of the CT complex and the amount used, to obtain electrically conductive or antistatically treated plastics materials, the CT complex being present in the form of a network of crystal needles in the plastics matrix. Depending on the concentration of the CT complex in the plastics matrix, very fine-meshed needle networks can be obtained.

The invention relates also to a composition comprising a) a thermosetting, thermoplastic or structurally crosslinked polymer and b) a CT complex of formula I in the form of a network of crystal needles in the polymer matrix.

The CT complexes may be present in an amount of from 0.01 to 30% by weight, preferably from 0.01 to 20% by weight, especially preferably from 0.01 to 10% by weight, and most preferably from 0.1 to 5% by weight, based on the composition.

The thermoplastic polymers may be, for example, the following polymers, copolymers or mixtures of these polymers:

1. Polymers of mono- and di-olefins, for example polypropylene, polyisobutylene, polybutene-1, polymethylpentene-1, polyisoprene or polybutadiene, as well as polymers of cycloolefins, for example of cyclopentene or norbornene; also polyethylene (which may be crosslinked), for example high-density polyethylene (HDPE), low-density polyethylene (LDPE), linear low-density polyethylene (LLDPE).

2. Mixtures of the polymers mentioned under 1), for example mixtures of polypropylene with polyisobutylene, polypropylene with polyethylene (e.g. PP/HDPE, PP/LDPE) and mixtures of different types of polyethylene (e.g. LDPE/HDPE).

3. Copolymers of mono- and di-olefins with one another or with other vinyl monomers, for example ethylene-propylene copolymers, linear low-density polyethylene (LLDPE) and mixtures thereof with low-density polyethylene (LDPE), propylene-butene-1 copolymers, propylene-isobutylene copolymers, ethylene-butene-1 copolymers, ethylenehexene copolymers, ethylene-methylpentene copolymers, ethylene-heptene copolymers, ethylene-octene copolymers, propylene-butadiene copolymers, isobutylene-isoprene copolymers, ethylene-alkyl acrylate copolymers, ethylene-alkyl methacrylate copolymers, ethylene-vinyl acetate copolymers or ethylene-acrylic acid copolymers and the salts thereof (ionomers), as well as terpolymers of ethylene with propylene and a diene, such as hexadiene, dicyclopentadiene or ethylidenenorbornene; also mixtures of such copolymers with one another and with polymers mentioned under 1), for example polypropylene/ethylene-propylene copolymers, LDPE/ethylene-vinyl acetate copolymers, LDPE/ethylene-acrylic acid copolymers, LLDPE/ethylene-vinyl acetate copolymers and LLDPE/ethylene-acrylic acid copolymers.

3a. Hydrocarbon resins (e.g. $C_5$–$C_9$) including hydrogenated modifications thereof (e.g. tackifying resins).

4. Polystyrene, poly-(p-methylstyrene), poly-($\alpha$-methylstyrene).

5. Copolymers of styrene or $\alpha$-methylstyrene with dienes or acrylic derivatives, for example styrene-butadiene, styrene-acrylonitrile, styrene-alkyl methacrylate, styrene-butadiene-alkyl acrylate, styrene-maleic acid anhydride, styrene-acrylonitrile-methyl acrylate; mixtures of high impact strength comprising styrene copolymers and another polymer, for example a polyacrylate, a diene polymer or an ethylene-propylene-diene terpolymer, also block copolymers of styrene, for example styrene-butadiene-styrene, styrene-isoprene-styrene, styrene-ethylene/butylene-styrene or styrene-ethylene/propylene-styrene.

6. Graft copolymers of styrene or $\alpha$-methylstyrene, for example styrene on polybutadiene, styrene on polybutadiene-styrene or polybutadiene-acrylonitrile copolymers, styrene and acrylonitrile (or methacrylonitrile) on polybutadiene; styrene, acrylonitrile and methyl methacrylate on polybutadiene; styrene and maleic acid anhydride on polybutadiene; styrene, acrylonitrile and maleic acid anhydride or maleic acid imide on polybutadiene; styrene and maleic acid imide on polybutadiene, styrene and alkyl acrylates or alkyl methacrylates on polybutadiene, styrene and acrylonitrile on ethylene-propylene-diene terpolymers, styrene and acrylonitrile on polyalkyl acrylates or polyalkyl methacrylates, styrene and acrylonitrile on acrylate-butadiene copolymers, as well as mixtures thereof with the copolymers mentioned under 5), such as are known, for example, as so-called ABS, MBS, ASA or AES polymers.

7. Halogen-containing polymers, for example polychloroprene, chlorinated rubber, chlorinated or chlorosulfonated polyethylene, copolymers of ethylene and chlorinated ethylene, epichlorohydrin homo- and co-polymers, especially polymers of halogen-containing vinyl compounds, for example polyvinyl chloride, polyvinylidene chloride, polyvinyl fluoride, polyvinylidene fluoride; and the copolymers thereof, such as vinyl chloride-vinylidene chloride, vinyl chloride-vinyl acetate or vinylidene chloride-vinyl acetate.

8. Polymers derived from $\alpha,\beta$-unsaturated acids and derivatives thereof, such as polyacrylates and polymethacrylates, polyacrylamides and polyacrylonitriles.

9. Copolymers of the monomers mentioned under 8) with one another or with other unsaturated monomers, for example acrylonitrile-butadiene copolymers, acrylonitrile-alkyl acrylate copolymers, acrylonitrile-alkoxyalkyl acrylate copolymers, acrylonitrile-vinyl halide copolymers, or acrylonitrile-alkyl methacrylate-butadiene terpolymers.

10. Polymers derived from unsaturated alcohols and amines or their acyl derivatives or acetals, such as polyvinyl alcohol, polyvinyl acetate, polyvinyl stearate, polyvinyl benzoate, polyvinyl maleate, polyvinylbutyral, polyallyl phthalate, polyallylmelamine; as well as the copolymers thereof with olefins mentioned under paragraph 1.

11. Homo- and co-polymers of cyclic ethers, such as polyalkylene glycols, polyethylene oxide, polypropylene oxide, or the copolymers thereof with bisglycidyl ethers.

12. Polyacetals, such as polyoxymethylene, and those polyoxymethylenes which contain comonomers, for example ethylene oxide; polyacetals modified by thermoplastic polyurethanes, acrylates or MBS.

13. Polyphenylene oxides and polyphenylene sulfides and mixtures thereof with styrene polymers or polyamides.

14. Polyurethanes derived on the one hand from polyethers, polyesters and polybutadienes having terminal hydroxy groups and on the other hand from aliphatic or aromatic polyisocyanates, and precursors thereof.

15. Polyamides and copolyamides derived from diamines and dicarboxylic acids and/or from aminocarboxylic acids or the corresponding lactams, such as polyamide 4, polyamide 6, polyamide 6/6, 6/10, 6/9, 6/12, 4/6, polyamide 11, polyamide 12, aromatic polyamides starting from m-xylylenediamine and adipic acid; polyamides prepared from hexamethylenediamine and iso- and/or terephthalic acid and, optionally, an elastomer as modifier, for example poly-2,4,4-trimethylhexamethyleneterephthalamide, and poly-m-phenyleneisophthalamide. Block copolymers of the above-mentioned polyamides with polyolefins, olefin copolymers, ionomers or chemically bonded or grafted elastomers; or with polyethers, for example with polyethylene glycol, polypropylene glycol or polytetramethylene glycol. Also polyamides or copolyamides modified by EPDM or ABS; as well as polyamides condensed during processing ("RIM polyamide systems").

16. Polyureas, polyimides, polyamide-imides and polybenzimidazoles.
17. Polyesters derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, polyhydroxy benzoates, as well as block polyether esters derived from polyethers containing hydroxy end groups; also polyesters modified by polycarbonates or MBS.
18. Polycarbonates and polyester carbonates.
19. Polysulfones, polyether sulfones and polyether ketones.
20. Polyethers from diglycidyl compounds, for example diglycidyl ethers and diols, for example from the diglycidyl ether of bisphenol A and bisphenol A.
21. Natural polymers, such as cellulose, natural rubber, gelatin, and their derivatives chemically modified in a polymer-homologous manner, such as cellulose acetates, propionates and butyrates, or the cellulose ethers, such as methylcellulose; as well as rosin resins and derivatives.
22. Mixtures (polyblends) of the above-mentioned polymers, for example PP/EPDM, polyamide-/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

Preferred thermoplastics are polyolefins, polystyrene, polyvinyl chloride, polyvinylidene chloride, polyvinylidene fluoride, polyacrylates, polymethacrylates, polyamides, polyesters, polycarbonates, aromatic polysulfones, aromatic polyethers, aromatic polyether sulfones, polyimides and polyvinylcarbazole.

The thermosetting polymers and structurally crosslinked polymers may be, for example, the following polymers:

1. Crosslinked polymers derived on the one hand from aldehydes and on the other hand from phenols, urea or melamine, such as phenol-formaldehyde, urea-formaldehyde and melamine-formaldehyde resins.
2. Drying and non-drying alkyd resins.
3. Unsaturated polyester resins derived from copolyesters of saturated and unsaturated dicarboxylic acids with polyhydric alcohols, as well as vinyl compounds as crosslinking agents, and also their halogen-containing, poorly combustible modifications.
4. Crosslinkable acrylic resins derived from substituted acrylic acid esters, for example from epoxy acrylates, urethane acrylates or polyester acrylates.
5. Alkyd resins, polyester resins and acrylate resins crosslinked with melamine resins, urea resins, polyisocyanates or epoxy resins.
6. Rubber based on crosslinked polydienes, for example butadiene or isoprene; silicone rubber.
7. Epoxy resins which are derived from polyepoxides, for example from bisglycidyl ethers of polyols or from cycloaliphatic diepoxides, and which may contain a hardener as crosslinking agent, or which are crosslinked thermally or by the action of radiation, using curing accelerators.

Of the crosslinked polymers, preference is given to crosslinked epoxy resins which, as polyepoxides, are preferably based on glycidyl compounds having an average of two epoxy groups in the molecule. Suitable glycidyl compounds are especially those having two glycidyl groups, β-methylglycidyl groups or 2,3-epoxycyclopentyl groups bonded to a hetero atom (e.g. sulfur, preferably oxygen or nitrogen); special mention may be made of bis(2,3-epoxycyclopentyl) ether; diglycidyl ethers of polyhydric aliphatic alcohols, such as 1,4-butanediol, or polyalkylene glycols, such as polypropylene glycols; diglycidyl ethers of cycloaliphatic polyols, such as 2,2-bis(4-hydroxycyclohexyl)propane; diglycidyl ethers of polyvalent phenols, such as resorcinol, bis(p-hydroxyphenyl)methane, 2,2-bis(p-hydroxyphenyl)propane (=diomethane), 2,2-bis(4'-hydroxy-3',5'-dibromophenyl)propane, 1,3-di(p-hydroxyphenyl)ethane; di(β-methylglycidyl) ethers of the dihydric alcohols or divalent phenols mentioned above; diglycidyl esters of dicarboxylic acids, such as phthalic acid, terephthalic acid, Δ$_4$-tetrahydrophthalic acid and hexahydrophthalic acid; N,N-diglycidyl derivatives of primary amines and amides and heterocyclic nitrogen bases containing two N atoms, and N,N'-diglycidyl derivatives of di-secondary diamides and diamines such as N,N-diglycidylaniline, N,N-diglycidyltoluidine, N,N-diglycidyl-p-aminophenyl-methyl ether, N,N'-dimethyl-N,N'-diglycidyl-bis(p-aminophenyl)methane; N',N''-diglycidyl-N-phenyl isocyanurate; N,N'-diglycidylethyleneurea; N,N'-diglycidyl-5,5-dimethylhydantoin, N,N'-diglycidyl-5-isopropyl-hydantoin, N,N-methylene-bis(N',N'-diglycidyl-5,5-dimethylhydantoin), 1,3-bis(N-glycidyl-5,5-dimethyl-hydantoin)-2-hydroxypropane; N,N'-diglycidyl-5,5-dimethyl-6-isopropyl-5,6-dihydro-uracil, triglycidyl isocyanurate.

A preferred group of epoxy resins comprises glycidylated novolaks, hydantoins, aminophenols, bisphenols and aromatic diamines or cycloaliphatic epoxy compounds. Especially preferred epoxy resins are glycidylated cresol novolaks, diglycidyl ether of bisphenol A and bisphenol F, hydantoin N,N'-bisglycide, p-aminophenol triglycide, diaminodiphenylmethane tetraglycide, vinylcyclohexene dioxide, 3,4-epoxycyclohexylmethyl-3,4-epoxycyclohexanecarboxylate, or mixtures thereof.

Also suitable are pre-reacted adducts of such epoxy compounds with epoxy hardeners, for example an adduct of the diglycidyl ether of bisphenol A and bisphenol A, or adducts pre-reacted with oligo esters having two terminal carboxy groups and epoxides.

Suitable hardeners for epoxy resins are acid or basic compounds. Examples of suitable hardeners which may be mentioned are: polyvalent phenols (resorcinol, 2,2-bis(4-hydroxyphenyl)propane) or phenol-formaldehyde resins; polybasic carboxylic acids and their anhydrides, for example phthalic acid anhydride, tetrahydrophthalic acid anhydride, hexahydrophthalic acid anhydride, 4-methylhexahydrophthalic acid anhydride, 3,6-endomethylene-tetrahydrophthalicacid anhydride, 4-methyl-3,6-endomethylene-tetrahydrophthalic acid anhydride (methylnadic anhydride), 3,4,5,6,7,7-hexachloro-endo-methylene-tetrahydrophthalic acid anhydride, succinic acid anhydride, adipic acid anhydride, trimethyladipic acid anhydride, sebacic acid anhydride, maleic acid anhydride, dodecylsuccinic acid anhydride, pyromellitic acid dianhydride, trimellitic acid anhydride, benzophenonetetracarboxylic acid dianhydride, or mixtures of such anhydrides.

A preferred group of hardeners comprises novolaks and polycarboxylic acid anhydrides.

The epoxy resins may also additionally be cured with curing accelerators or only with heat curing catalysts. Examples are 3-ethyl-4-methylimidazole, triamylammonium phenolate; mono- or poly-phenols (phenol, diomenthane, salicylic acid); boron trifluoride and its complexes with organic compounds, for example boron trifluoride-ether complexes and boron trifluoride-amine complexes (BF$_3$-monoethylamine complex); phosphoric acid and triphenyl phosphite.

Curing accelerators and catalysts are customarily added in an amount of from 0.1 to 10% by weight, based on the epoxy resin. Hardeners for epoxy resins are generally used in equimolar amounts, based on the epoxy groups and functional groups of a hardener.

It is possible to incorporate into the composition according to the invention further additives for improving the processing properties, the mechanical, electrical and thermal properties, the surface properties and the light stability, for example finely particulate fillers, reinforcing fillers, plasticisers, lubricants and mould-release agents, tackifiers, antistatic agents, antioxidants, heat and light stabilisers, pigments and colourings.

In a preferred embodiment, the composition according to the invention is in the form of a moulding, a film, a foil or a fibre, or is in the form of a coating on at least one surface of a substrate.

The invention relates also to a process for the preparation of compositions according to the invention, which comprises (a) incorporating a CT complex of formula I into a thermoplastic plastics material, (b) incorporating a CT complex of formula I into at least one component of a thermosetting or structurally crosslinkable plastics material and then polymerising the mixture, optionally together with further components, to form a thermosetting or structurally crosslinked plastics material, or (c) dissolving a compound of formula II, a 5,10-dihydrophenazine derivative or the iodine salt thereof as B or the iodine salt of an N-aromatic compound B, together with a thermoplastic plastics material or at least one component of a thermosetting or structurally crosslinkable plastics material, in an organic solvent, mixing that solution, optionally together with further components for a thermosetting or structurally crosslinkable plastics material, with a solution of a 5,10-dihydrophenazine derivative or the iodine salt thereof as B or of an iodine salt of an N-aromatic compound B or of a compound of formula II, removing the solvent, and polymerising curable mixtures to form a thermosetting or structurally crosslinked plastics material. The preparation process may be combined with a moulding operation.

The composition according to the invention can be prepared according to processes known in plastics technology. In the case of moulding processes for polymers, for example casting, compression moulding processes, injection moulding and extrusion, the CT complex itself may be added to a thermoplastic or at least one starting material for thermosetting plastics materials, to form suspensions, or it may be added separately to in each case one starting material (for example, the epoxy resin and the hardener) to form solutions or suspensions, and, after moulding, the CT complex crystallises out or precipitates during cooling in the form of needles which form a network in a polymer matrix.

In an especially preferred embodiment, the composition according to the invention is in the form of a film or foil or in the form of a coating on at least one surface of a substrate. To prepare such embodiments, for example, a thermoplastic polymer or at least one starting material for a thermosetting plastics material or a structurally crosslinked polymer is suspended and/or dissolved in an inert solvent together with a CT complex of formula I, or is dissolved together with a compound of formula II or an iodine salt of an N-aromatic compound B, and then there is added a solution of the N-aromatic iodine salt B or of a compound of formula H and the whole is mixed and then applied by means of known coating techniques to a substrate, which may be pre-heated, and then, with heating, the solvent is removed, it then being possible for crosslinkable mixtures to be cured fully. Unsupported films and foils are obtained by being detached from the substrate or by means of extrusion processes.

Suitable substrates are, for example, glass, metals, plastics materials, mineral and ceramic materials, wood and paper. The substrates may have any outer shape; they may be, for example, mouldings, threads, fibres, woven articles, rods, tubes, bands, foils, plates, rollers or housings.

Suitable coating methods are, for example, brushing, rolling, knife application, pouring, spin coating, curtain coating and spraying. Especially preferred methods are spray methods because, on the one hand, it is possible to obtain very thin and uniform layers with substantially isotropic, very fine-meshed and homogeneous networks of crystal needles of the CT complexes and, on the other hand, the size of the crystal needles and the mesh size of the networks can be controlled by the drop size, even when suspensions are sprayed.

Suitable inert solvents for polymers, or starting materials for polymers, are, for example, polar and, preferably, aprotic solvents, which may be used alone or in mixtures of at least two solvents. Examples are: ethers (anisole, dibutyl ether, tetrahydrofuran, dioxane, ethylene glycol monomethyl or dimethyl ether, ethylene glycol monoethyl or diethyl ether, diethylene glycol diethyl ether, triethylene glycol dimethyl ether), halogenated hydrocarbons (methylene chloride, chloroform, 1,2-dichloroethane, 1,1,1-trichloroethane, 1,1,2,2-tetrachloroethane), carboxylic acid esters and lactones (ethyl acetate, propionic acid methyl ester, benzoic acid ethyl ester, 2-methoxyethyl acetate, γ-butyrolactone, δ-valerolactone, pivalolactone), carboxylic acid amides and lactams (N,N-dimethylformamide, N,N-diethylformamide, N,N-dimethylacetamide, tetramethylurea, hexamethylphosphoric acid triamide, γ-butyrolactam, ε-caprolactam, N-methylpyrrolidone, N-acetylpyrrolidone, N-methylcaprolactam), ketones (methyl ethyl ketone, methyl isobutyl ketone), sulfoxides (dimethyl sulfoxide), sulfones (dimethylsulfone, diethylsulfone, trimethylenesulfone, tetramethylenesulfone), tertiary amines (N-methylpiperidine, N-methylmorpholine), substituted benzenes (benzonitrile, chlorobenzene, o-dichlorobenzene, 1,2,4-trichlorobenzene, nitrobenzene, toluene, xylene) and nitriles (acetonitrile, propionitrile). Also suitable are aromatic-aliphatic ethers, for example methyl- or ethyl-phenyl ethers. Suitable solvents for the compounds of formula II and the N-aromatic compounds/iodine salts B have been mentioned above.

The coating processes may, for example, be carded out by dissolving the individual components separately and combining them just before the chosen coating process. However, it is also possible to prepare the components in two solutions, for example polymer solution and N-aromatic iodine salt B or a compound of formula II and solution of a compound of formula II or of an N-aromatic iodine salt B, optionally together with a polymer, or to combine all the components in one solution. In the latter case, the CT complexes may crystallise out before the coating process, but that has virtually no effect on the desired quality of the coating.

The solutions are advantageously heated, for example to from 30° to 200° C. It is advantageous also to heat the substrate in order to accelerate removal of the solvent, which is generally carded out at temperatures of from 50° to 150° C., preferably from 50° to 100° C., until the coating is dry. If the coatings are to be detached to form unsupported films or foils, the substrate may be treated prior to the coating process with anti-adhesive agents.

In a preparation variant for coatings, it is also possible to suspend the CT complexes according to the invention, which are in the form of crystal needles, in a solution of a polymer or of starting materials for thermosetting plastics materials, then to coat a substrate and subsequently remove the solvent and, optionally, fully cure to form the thermosetting plastics materials. Moreover, it is possible to prepare powdered dry mixtures of polymer powders or solid starting materials for thermosetting plastics materials and the CT complexes and to process them in coating processes, which may be electrostatic, to form layers on substrates. In these variants, too, networks of crystal needles in a polymer matrix are obtained.

It is also possible to prepare pure layers of networks of crystal needles of the CT complexes on a substrate, by, for example, applying solutions or suspensions of the CT complexes in a solvent to d substrate and then evaporating off the solvent. Such layers may be metallised electrochemically, for example with Cu, Pt or Pd, in order to increase the electrical conductivity. It may be advantageous to coat such pure layers with a protecting layer of a polymer or subsequently to cover the pure layers with a polymer.

The layer thicknesses may vary within a wide range depending on the chosen coating method. With spray methods, very thin layers can be obtained, while with brushing and pouring methods it is also possible to obtain thick layers. The layer thicknesses may be, for example, from 0.01 to 5000 μm, preferably from 0.1 to 1000 μm and especially preferably from 0.1 to 500 μm.

The composition according to the invention is opaque or transparent, depending on the polymer chosen, and it has excellent electrical properties. For example, the coatings and mouldings surprisingly have an excellent discharge ability, which is otherwise difficult or impossible to achieve for heterogeneous materials. The compositions are therefore especially suitable for use in the form of antistatically treated mouldings for the electrostatic protection of components, or for use in the form of antistatically treated mouldings. Moreover, the high electrical conductivities allow them to be used as electrical conductors, for example as electrodes for display elements or electronic components and as charge carders in capacitors. The compositions also have excellent mechanical strength and mechanical properties in use. The compositions can also be prepared at comparatively low temperatures and, in addition, have the advantage of causing no or only insignificant corrosion to the metal pans of machines. Furthermore, they have good stability with respect to the effect of heat and/or moisture.

The invention relates also to the use of the charge-transfer complexes of formula I according to the invention as electrical conductors; to the use of the composition according to the invention in the form of antistatically treated mouldings for the electrostatic protection of components or in the form of antistatically treated mouldings; to the use of the composition according to the invention as electrical conductors; to the use of the composition according to the invention as electrode material; and to the use of the composition according to the invention in the form of films or foils as charge carriers in capacitors.

The following Examples illustrate the invention in more detail.

A) PREPARATION EXAMPLES

Example A 1: Preparation of N-Methylisoquinolinium 5,7,12,14-Tetracyanoiminepentacene To a solution of 100 mg (0.369 mmol) of N-methylisoquinolinium iodide in 40 ml of dimethylformamide (DMF) there is added, at room temperature, a filtered solution, having the same temperature, of 160 mg (0.369 mmol) of 5,7,12,14-tetracyanoiminepentacene in 60 ml of DMF. A dark-green solution is obtained, which is left to stand for 15 hours at 5° C. Then the resulting brown crystal needles are filtered off, washed with DMF and diethyl ether and then dried in vacuo, yielding 66.7 mg (31% yield) of the title compound, the electrical conductivity of which (measured by the four-point method on a moulding) is 0.034 S/cm. Elemental analysis found (calculated) for $C_{36}H_{20}N_9 \cdot DMF$: C 71.67 (71.88); H 4.22 (4.18); N 21.35 (21.49). Decomposition temperature 271° C.

Example A2: Preparation of N-methylquinolinium 5,7,12,14-tetracyanoiminepentacene To a solution of 100 mg (0.369 mmol) of N-methylquinolinium iodide in 20 ml of DMF there is added, at room temperature, a filtered solution of 160 mg (0.369 mmol) of 5,7,12,14-tetracyanoiminepentacene in 30 ml of DMF. A green solution is obtained, which is left to stand for 15 hours at 5° C. Then the resulting brown crystal needles are filtered off, washed with DMF and diethyl ether and dried in vacuo, yielding 110 mg (52% yield) of the title compound. The electrical conductivity (moulding) is 0.16 S/cm. Elemental analysis found (calculated) for $C_{36}H_{20}N_9$: C 74.55 (74.73); H 3.58 (3.48); N 21.78 (21.79). Decomposition temperature 266° C.

Example A3: Preparation of N-methylbenzopyridazinium 5,7,12,14-tetracyanoiminepentacene To a solution, having a temperature of 100° C., of 100 mg (0.367 mmol) of N-methylbenzopyridazinium iodide in 10 ml of γ-butyrolactone there is added a solution, having the same temperature, of 159 mg (0.367 mmol) of 5,7,12,14-tetracyanoiminepentacene in 50 ml of DMF. The solution is allowed to cool down to room temperature and is then left to stand for 15 hours at 5° C. Then the resulting green/black crystal needles are filtered off, washed with diethyl ether and dried in vacuo, yielding 213 mg (100% yield) of the title compound. The electrical conductivity (moulding) is 1.85 S/cm. Elemental analysis found (calculated) for $C_{35}H_{19}N_{10}$: C 71.81 (72.53); H 2.98 (3.30); N 24.73 (24.17). Decomposition temperature 273° C.

Example A4: Preparation of N-Methylpyrazinium 5,7,12,14-Tetracyanoiminepentacene To a solution, having a temperature of 100° C., of 77 mg (0.345 retool) of N-methylpyrazinium iodide in 30 ml of DMF there is added a solution, having the same temperature, of 150 mg (0.345 mmol) of 5,7,12,14-tetracyanoiminepentacene in 50 ml of DMF. A dark-red solution is obtained, which, after cooling to room temperature, yields a dark-green crystalline suspension. Filtering off and washing with diethyl ether yield 57 mg, and a further 42 mg of the title compound crystallise from the filtrate: total 99 mg (54% yield) of fine green crystal needles. The electrical conductivity (moulding) is 2.40 S/cm. Elemental analysis found (calculated) for $C_{31}H_{17}N_{10}$: C 70.28 (70.31); H 2.87 (3.24); N 26.08 (26.45). Decomposition temperature 240° C.

Example A5: Preparation of 5,10-Dimethyl-5,10-dihydrophenazinium 5,7,12,14-Tetracyanoiminepentacene To a solution, having a temperature of 110° C., of 100 mg (0.476 mmol) of 5,10-dimethyl-5,10-dihydrophenazine in 20 ml of anisole there is added a solution, having the same temperature, of 207 mg (0.476 mmol) of 5,7,12,14-tetracyanoiminepentacene in 70 ml of anisole. An orange solution is obtained, which, after cooling down to room temperature, is left to stand for 15 hours. Then the resulting brown crystal needles are filtered off, washed with anisole and dichloroethane and dried in vacuo, yielding 210 mg (68% yield) of the title compound. The electrical conductivity (moulding) is 0.082 S/cm. Elemental analysis found (calculated) for $C_{40}H_{24}N_{10}$: C 74.46 (74.52); H 4.01 (3.75); N 20.37 (21.73). Decomposition temperature 297° C.

B) APPLICATION EXAMPLE

Example B 1

A solution, having a temperature of 130° C., of 4.5 mg of 5,7,12,14-tetracyanoiminepentacene in 7 ml of anisole is added to a solution, having a temperature of 130° C., of 200 mg of polycarbonate and 2.1 mg (0.01 mmol) of 5,10-dimethyl-5,10-dihydrophenazine in 7 ml of anisole. Aliquot portions (in each case 2 ml) are poured onto a glass plate and then the solvent is evaporated off at different temperatures. The conductivity of the resulting foils is then measured.

| Evaporation temperature (°C.) | Conductivity (S/cm) |
| --- | --- |
| 100 | $2.3 \cdot 10^{-4}$ |
| 110 | $2.1 \cdot 10^{-4}$ |

What is claimed is:

1. An electrically conductive crystal network consisting of needle shaped crystals of a charge-transfer complex of formula I $$(A^{\ominus})_n B^{n\oplus} \quad (I)$$

wherein
a) n is 1 or 2,
b) A is the radical anion of a compound of formula II or of a mixture of compounds of formula II

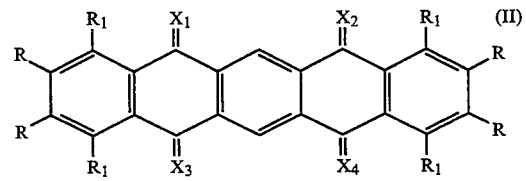

wherein the substituents R are the same and are H or $C_1$-$C_4$alkyl, or adjacent substituents R together form —$(CH_2)_3$— or —$(CH_2)_4$—;
$R_1$ is H or $C_1$-$C_4$alkyl;
$X_1$ is =N—CN; and
$X_2$, $X_3$ and $X_4$ are =O or =N—CN, and
c) when n=1, B is the monovalent radical cation, or, when n=2, B is the divalent radical cation of an N-aromatic compound having a total of from 1 to 5 aromatic rings that are unsubstituted or substituted by halogen, $C_1$-$C_4$alkyl or by $C_1$-$C_4$alkoxy, at least one N-heterocyclic ring containing at least one group —$NR_2$— or [=$N^+R_2$—] $I^-$ wherein $R_2$ is $C_1$-$C_4$alkyl or benzyl.

2. A network according to claim 1 wherein R is $C_1$-$C_4$alkyl and $R_1$ is H.

3. A network according to claim 1 wherein $R_1$ is $C_1$-$C_4$alkyl and R is H.

4. A network according to claim 1 wherein R and $R_1$ are methyl or ethyl.

5. A network according to claim 1 wherein R and $R_1$ are H, methyl or ethyl.

6. A network according to claim 1 wherein R and $R_1$ are H.

7. A network according to claim 1 wherein $X_1$ and $X_4$ are =N—CN and $X_2$ and $X_3$ are =O or =N—CN, or $X_2$ and $X_3$ are =N—CN and $X_4$ is =O or =N—CN.

8. A network according to claim 1 wherein $X_1$, $X_2$, $X_3$ and $X_4$ are =N—CN.

9. A network according to claim 1 wherein N-heterocyclic rings of the cation B contain 1 or 2N atoms.

10. A network according to claim 1 wherein B in formula I corresponds to cations of formulae IIIa to IIIf:

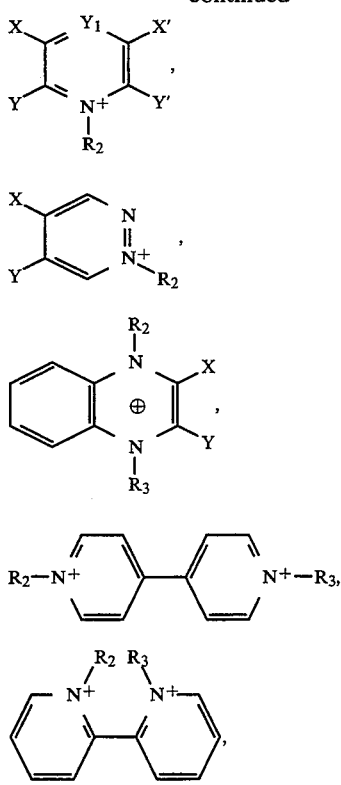

wherein
Y₁ is N or CH, and
X, X', Y and Y' are H, or
X and Y and/or X' and Y' are the group —CH=CH—CH=CH—, and
R₃ independently has the same meaning as R₂.

11. A network according to claim 10 wherein R₂ and R₃ are methyl or ethyl.

12. A network according to claim 10 wherein B is a cation of N-methyl- or N-ethyl-pyridinium; N-methyl- or N-ethyl-pyrazinium; N-methyl- or N-ethyl-quinolinium; N-methyl- or N-ethyl-phthalazinium; N-methyl- or N-ethyl-isoquinolinium; N-methyl- or N-ethyl-benzopyrazinium; 4,4'-dimethyl-, 4,4'-diethyl- or 4-methyl-4'-ethyl-bipyridinium; N-methyl- or N-ethyl-acridinium; N-methyl- or N-ethyl-phenazinium; 2,2'-dimethyl-, 2,2'-diethyl- or 2-methyl-2'-ethyl-bipyridinium; N-methyl- or N-ethyl-pyridazinium; 5,10-dimethyl-, 5,10-diethyl- or 5-methyl- 10-ethyl-5,10-dihydrophenazinium.

13. A network according to claim 1 wherein, in formula I, A is 5,7,12,14-tetracyanoiminepentacene and B is N-methylpyrazinium, N-ethylpyrazinium, 5,10-dimethyl-5,10-dihydrophenazinium, N-methylquinolinium, N-methylisoquinolinium or N-methylbenzopyridazinium.

14. A process for the preparation of a charge-transfer complex of formula I according to claim 1, which comprises reacting one equivalent of a neutral unsubstituted or substituted 5,10-dihydrophenazine or the iodine salt thereof as B, or the iodine salt of an N-aromatic compound B, with at least one equivalent of a pentacenecyanoimine of formula II in an inert organic solvent.

15. A composition comprising a) a thermosetting, thermoplastic or structurally crosslinked polymer and b) a charge-transfer complex of formula I according to claim 1 in the form of a network of crystal needles in the polymer matrix.

16. A composition according to claim 15 wherein the charge-transfer complex is present in an amount of from 0.01 to 30% by weight, based on the composition.

17. A composition according to claim 16 wherein the charge-transfer complex is present in an amount of from 0.01 to 10% by weight.

18. A composition according to claim 15 wherein the thermoplastic polymer is a polyolefin, polystyrene, polyvinyl chloride, polyvinylidene chloride, polyvinylidene fluoride, polyacrylate, polymethacrylate, polyamide, polyester, polycarbonate, aromatic polysulfone, aromatic polyether, aromatic polyether sulfone, polyimide or polyvinylcarbazole.

19. A composition according to claim 15 wherein the thermosetting polymer is an epoxy resin.

20. A composition according to claim 15 which is in the form of a moulding, a film, a foil or a fibre, or is in the form of a coating on at least one surface of a substrate.

21. A composition according to claim 20 wherein the layer thickness of the coating is from 0.01 to 5000 μm.

22. A composition according to claim 20 wherein the layer thickness of the coating is from 0.1 to 1000 μm.

23. A process for the preparation of a composition according to claim 15, which comprises
(a) incorporating a CT complex of formula I into a thermoplastic plastics material,
(b) incorporating a CT complex of formula I into at least one component of a thermosetting or structurally crosslinkable plastics material and then polymerising the mixture, optionally together with further components, to form a thermosetting or structurally crosslinked plastics material, or
(c) dissolving a compound of formula II or an unsubstituted or substituted 5,10-dihydrophenazine or the iodine salt thereof as B or an iodine salt of the N-aromatic compound B, together with a thermoplastic plastics material or at least one component of a thermosetting or structurally crosslinkable plastics material, in an organic solvent, mixing that solution, optionally together with further components for a thermosetting or structurally crosslinkable plastics material, with a solution of an unsubstituted or substituted 5,10-dihydrophenazine or the iodine salt thereof as B or of the iodine salt of an N-aromatic compound B or of a compound of formula II, removing the solvent, and polymerising curable mixtures to form a thermosetting or structurally crosslinked plastics material.

24. A process according to claim 23 which is combined with a moulding operation.

* * * * *